US008642613B2

(12) United States Patent
Kallick

(10) Patent No.: US 8,642,613 B2
(45) Date of Patent: Feb. 4, 2014

(54) TREATMENT FOR LEUKEMIA AND IDIOPATHIC APLASTIC ANEMIA

(75) Inventor: Charles A. Kallick, Chicago, IL (US)

(73) Assignee: Sphingomonas Research Partners, L.P., Chicago, IL (US)

( * ) Notice: Subject to any disclaimer, the term of this patent is extended or adjusted under 35 U.S.C. 154(b) by 894 days.

(21) Appl. No.: 12/561,938

(22) Filed: Sep. 17, 2009

(65) Prior Publication Data

US 2010/0204217 A1     Aug. 12, 2010

Related U.S. Application Data

(60) Provisional application No. 61/097,760, filed on Sep. 17, 2008.

(51) Int. Cl.
*A61K 31/343*  (2006.01)
*A61K 31/395*  (2006.01)
*A61P 35/00*   (2006.01)

(52) U.S. Cl.
USPC ............ 514/279; 514/299; 514/312; 514/450

(58) Field of Classification Search
USPC ............ 514/230.2, 278, 253.08, 254.11, 279, 514/299, 312, 450
See application file for complete search history.

(56) References Cited

U.S. PATENT DOCUMENTS

| 5,928,879 A | 7/1999 | Dumler et al. |
| 2005/0143409 A1 | 6/2005 | Michaelis et al. |
| 2007/0238747 A1 | 10/2007 | Van Duzer et al. |

FOREIGN PATENT DOCUMENTS

WO    WO 2006/050457    5/2006

OTHER PUBLICATIONS

Burghouts, "A possible role of rifampicin in prolonging remission duration in acute myelogenous leukaemia", Scand J Haematol., Apr. 1986, 36(4), pp. 376-378.*
Kissling, "Effect of fleroxacin and ciprofloxacin on the formation of human mature colonies of healthy donor versus transplanted hemopoietic progenitor cells", Chemotherapy, 1991, 37(3), pp. 212-217.*
Dr. Kallick's Declaration Kallick, *Medical Hypotheses* 77 (2011) 374-379.
Appelbaum, "The Acute Leukemias", Cecil Textbook of Medicine, $20^{th}$ Ed. vol. 1, pp. 963-940 (1996).
Sonneveld et al., *Blood* 79(6):1496-1500 (1992).
Kissling et al., *Chemotherapy* 37:212-217 (1991).
Run-sheng et al., *Chin Med J* 102(9):695-697 (1989).
Kashimoto et al;.*Proc Am Assoc Cancer Res* 42:102(2001).
PCT International Search Report PCT/US 09/57340.
PCT Written Opinion PCT/US 09/57340.
Supplementary European Search Report EP 09815209 (PCT/US 09/57340).
IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updated compiled by A. Jenkins. ISBN.

* cited by examiner

*Primary Examiner* — Sreeni Padmanabhan
*Assistant Examiner* — Sahar Javanmard
(74) *Attorney, Agent, or Firm* — Husch Blackwell, LLP

(57) ABSTRACT

A process for treating a patient with leukemia or an aplastic anemia having cells with inclusions that stain with anti-*E. canis* antibodies or antibodies to other *Ehrlichia* or *Anaplasma* is disclosed. That process comprises administering to the patient (i) an antibacterial amount of a rifamycin, (ii) an antibacterial amount of a quinolone, or a mixture of (i) and (ii).

10 Claims, 5 Drawing Sheets

Increases in platelets over time in thousands
Normal platelets = 150-400k
Platelets before therapy = 11k Increases in white cell counts over time in hundreds
Normal white count = 4000 - 12,000
White cells before therapy = 900

TREATMENT FOR LEUKEMIA AND IDIOPATHIC APLASTIC ANEMIA

CROSS-REFERENCE TO RELATED APPLICATION

This application claims priority from U.S. Ser. No. 61/097,760 filed Sep. 17, 2008, and whose disclosures are incorporated herein by reference.

TECHNICAL FIELD

The present invention relates to the treatment of leukemias and idiopathic aplastic anemia in humans, and more particularly to treating those diseases as bacterial infections of blood and marrow cells using strong antibiotics.

BACKGROUND ART

Leukemia is a name for a group of diseases that are cancers of the marrow and blood. The two major groups are lymphatic, and myeloid leukemia. Both groups are considered as either acute or chronic depending on various factors. Also included are lymphoid leukemias. Leukemias can thus be divided into four main types: acute lymphocytic leukemia, acute myelogenous leukemia, chronic lymphocytic leukemia and chronic myelogenous leukemia. Acute and chronic leukemias are usually studied as groups separated by the cells which are affected.

These heterogeneous groups are usually considered together and are considered as a group of diseases characterized by infiltration of the bone marrow and other tissues by the cells of the hematopoetic system. The infiltration is called neoplastic, meaning new growth of cells, but all of the cells seen in the marrow, and peripheral circulation in leukemia are normal in a normal bone marrow, except for one structure, seen in myelocytic leukemia called Auer rods. These structures are repeated in this kind of leukemia, and are unknown as to structure, and relationship to any other material.

The majority of patients with leukemia are not cured with standard chemotherapy. There is no therapy that is considered standard of care in patients with relapsed acute lymphocytic leukemia. Because the median age is 70 years in the U.S., the majority of patients are not eligible for allogeneic stem cell transplantation, which is the only known cure for patients with relapsed or refractory acute leukemia. Although there are various investigational agents available, the response rates are small, duration of response short and adverse events sometimes unacceptable. Thus, there is an unmet need for new agents in this group of patients who are otherwise managed with supportive care only.

An adult human has about 7000 white blood cells per microliter (µl) of blood. Of those white cells, about 65 percent are granulocytes (about 4500/µl), about 30 percent are monocytes (about 2100/µl) and about five percent are lymphocytes (about 350/µl) [Geyton, *Textbook of Medical Physiology*, Seventh ed., W. B. Saunders Co., Philadelphia (1986)]. The above cell numbers are, of course, generalized average values, and granulocyte counts for normal patients typically range from about 2000 to about 7000 cells/µl.

Chronic myelogenous leukemia (CML), also known as chronic granulocytic leukemia (CGL), is a neoplastic disorder of the hematopoietic stem cell. In its early phases, this disease is characterized by leukocytosis, the presence of increased numbers of immature granulocytes in the peripheral blood, splenomegaly and anemia. These immature granulocytes include basophils, eosinophils, and neutrophils. The immature granulocytes also accumulate in the bone marrow, spleen, liver, and occasionally in other tissues. Patients presenting with this disease characteristically have more than 75,000 white blood cells per microliter, and the count may exceed 500,000/µl. Cytologically, CML is characterized by a translocation between chromosome 22 and chromosome 9. This translocation juxtaposes a purported proto-oncogene with tyrosine kinase activity, a circumstance that apparently leads to uncontrolled cell growth. The resulting translocated chromosome is sometimes referred to as the Philadelphia chromosome.

CML accounts for about 20 percent of all leukemias in the United States. About 15 new cases per million people are reported each year, leading to about 3,000 to 4,000 new cases per year. The disease is rare in humans below age 45, rises rapidly to age 65, and remains high thereafter. The median life span of patients with chronic myelogenous leukemia from the time of diagnosis is approximately four years.

Patients with chronic CML have usually been treated with alkylating agents such as busulfan or by treatment with hydroxyurea. In recent years treatment with α-interferon has been used.

About 60 to 80 percent of patients with CML develop a blast crisis. This blast crisis represents a manifestation of acute leukemia. The presence of certain markers on the blast cells sometimes suggests a lymphoid origin of these cells during the blast crisis. Chemotherapeutic agents used for the treatment of the blast crisis are the same as those used for the treatment of other acute leukemias. However, these drug therapies of the blast crisis stage of CML are even less successful than are the treatments of other acute leukemias.

Chronic lymphocytic leukemia (also known as "chronic lymphoid leukemia" or "CLL"), is a leukemia of the white blood cells (lymphocytes) that affects a particular lymphocyte, the B cell, which originates in the bone marrow, develops in the lymph nodes, and normally fights infection. In CLL, the DNA of a B cell is damaged, so that it cannot fight infection, but grows out of control and crowds out the healthy blood cells that can fight infection.

CLL is an abnormal neoplastic proliferation of B cells. The cells accumulate mainly in the bone marrow and blood. Although not originally appreciated, CLL is now thought to be identical to a disease called small lymphocytic lymphoma (SLL), a type of non-Hodgkin's lymphoma which presents primarily in the lymph nodes. The World Health Organization considers CLL and SLL to be "one disease at different stages, not two separate entities". [Harris et al., (1999) "World Health Organization classification of neoplastic diseases of the hematopoietic and lymphoid tissues: report of the Clinical Advisory Committee meeting-Airlie House, Virginia, November 1997", *J. Clin. Oncol.* 17(12):3835-3849.]

CLL is a disease of adults. Most (>75%) people newly diagnosed with CLL are over the age 50, and the majority are men. In the United States during 2007, it is estimated there will be 15,340 new cases diagnosed and 4,500 deaths [National Cancer Institute. "Chronic Lymphocytic Leukemia (PDQ) Treatment: General Information", Retrieved on 2007-09-04] but because of prolonged survival, many more people are living with CLL.

Most people are diagnosed without symptoms as the result of a routine blood test that returns a high white blood cell count, but as it advances, CLL results in swollen lymph nodes, spleen, and liver, and eventually anemia and infections. Early CLL is not usually treated, and late CLL is treated with chemotherapy and monoclonal antibodies. Survival varies from 5 years to more than 25 years. It is now possible to diagnose patients with short and long survival more precisely by examining the DNA mutations, and patients with slowly-progressing disease can be reassured and may not need any treatment in their lifetimes [Chiorazzi et al., (2005) *N. Engl. J. Med.* 352(8):804-815].

Acute lymphocytic leukemia (ALL) is also referred to as acute lymphoblastic leukemia and acute lymphoid leukemia. About 5,430 people in the United States are expected to be diagnosed with ALL in 2008 [The Leukemia & Lymphoma Society web site updated Jul. 14, 2008]. It is the most common type of leukemia in children under age 15. The risk of getting ALL increases in people ages 45 and older. However, people can get ALL at any age. Most children with ALL are cured of their disease after treatment.

ALL is said by the The Leukemia & Lymphoma Society to start with a change to a single cell in the bone marrow. The exact genetic changes that cause a normal cell to become an ALL cell are being studied. Few factors have been associated with an increased risk of developing ALL. Exposure to high doses of radiation therapy used to treat other types of cancer is one known risk factor. Other possible risk factors are continually under study. ALL is said not to be contagious [The Leukemia & Lymphoma Society web site updated Jul. 14, 2008].

Aplastic anemia is a condition in which bone marrow does not produce sufficient new cells to replenish blood cells. Aplastic anemia typically results from injury to blood stem cells. Normal blood stem cells divide and differentiate into all blood cell types. Thus, when blood stem cells are injured, there is a reduction in red blood cells, white blood cells, and platelets.

Aplastic anemia can be caused by chemotherapy, drug therapy to suppress the immune system, radiation therapy, toxins such as benzene or arsenic, drugs, pregnancy, and disorders present birth. When the cause is unknown, it is then referred to as idiopathic aplastic anemia. The disease can be acute or chronic and usually gets worse unless the cause is removed.

The term 'aplastic' means the marrow suffers from an aplasia that renders it unable to function properly. Anemia is the condition of having reduced hemoglobin or red cell concentration in the blood. Typically, anemia refers to low red blood cell counts, but aplastic anemia patients have lower counts of all three blood cell types: red blood cells, white blood cells, and platelets, or pancytopenia.

This disease is characterized by the following symptoms: 1) a low red blood cell count (anemia) leads to fatigue and weakness; 2) a low white blood cell count (leukopenia) leads to frequent or severe infections; 3) a low platelet count (thrombocytopenia) that can result in easy bruising, nose bleeds, bleeding of the gums, and bleeding of internal organs. Other symptoms include shortness of breath during physical activity, rapid heart rate, and rash. Identifying assays include one or more of the following: a complete blood count (CBC) that shows low hematocrit and hemoglobin levels (anemia); a reticulocyte count that is low; a low platelet count; a low white blood cell count; and a bone marrow biopsy that shows very few cells.

Rifampicin, or rifampin, below, is a drug whose

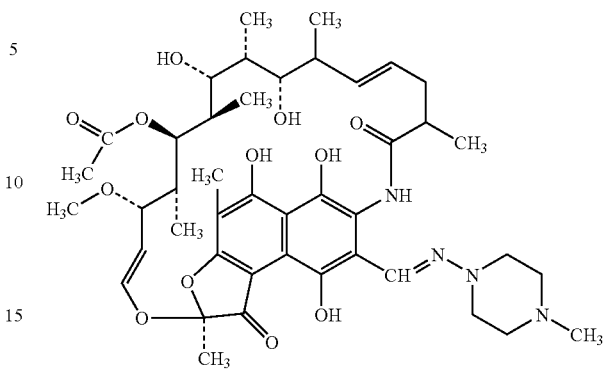

use has been approved for infections caused by a great number of infectious agents. Its action appears to be an effect on DNA-dependent RNA polymerase activity of bacterial infections. Rifampicin is useful for gram negative bacteria such as *Neiseria meningitides*, and *M. tuberculosis*.

Rifampicin is also effective against intracellular bacterial pathogens. Rifampicin is particularly effective against intracellular organisms in the genus of *Ehrlich/Anaplasma*, for which it appears to be the only effective antibiotic, with tetracycline being less effective and bacteriostatic.

BRIEF SUMMARY OF THE INVENTION

The present invention contemplates a process for treating a patient with leukemia or an aplastic anemia having cells with inclusions that stain with anti-*E. canis* antibodies. That process comprises administering to the patient an antibacterial agent that is (i) an antibacterial amount of a rifamycin, (ii) an antibacterial amount of a quinolone, or a mixture of i and ii. In preferred practice, the rifamycin is one or more of rifampin, rifabutin or rifamide, and the quinolone compound is selected from one or more of the group consisting of nalidixic acid, ciprofloxacin, levofloxacin, moxifloxacin, gatifloxacin, tefloxacin and trovafloxacin.

The patient's marrow cells and/or erythrocytes typically contain bacterial structures stainable with acridine orange or giemsa that are also visible in phase contrast microscopy once stained. In preferred practice, the antibacterial agent administration is repeated periodically until the bacterial structures are eliminated from the patient's marrow cells and/or erythrocytes or both.

BRIEF DESCRIPTION OF THE DRAWINGS

In the drawings forming a part of this invention,

FIG. 5 is a photomicrograph of a peripheral cell from a patient with myelocytic leukemia, and Auer rods. The stain is anti-*E. canis* antibodies. The photograph was taken to show that the presumed Auer rod was in this cell and stained with the fluorescent antibody. Also in the cell are inclusions which appear to be morula-like.

DETAILED DESCRIPTION OF THE INVENTION

Figure 1:
FIG. 1 is a photomicrograph of a macrophage from a patient with aplastic anemia that was stained with a direct conjugate of anti-*E. canis* antibodies (Courtesy of Dr. M Nyindo and the late Dr. M. Ristic).

The present invention contemplates a process for treating a patient with leukemia or an aplastic anemia having cells with inclusions that stain with anti-*E. canis* antibodies or antibodies to other *Ehrlichia* or *Anaplasma*. That process comprises administering to the patient an antibacterial agent that is (i) an antibacterial amount of a rifamycin, (ii) an antibacterial amount of a quinolone, or a mixture of i and ii. In preferred practice, the rifamycin is one or more of rifampin, rifabutin or rifamide, and the quinolone compound is selected from one or more of the group consisting of nalidixic acid, ciprofloxacin, levofloxacin, moxifloxacin, gatifloxacin, tefloxacin and trovafloxacin.

The leukemia patient's marrow cells and/or erythrocytes typically contain bacterial structures stainable with acridine orange or giemsa that are visible in phase contrast microscopy once stained. In preferred practice, the antibacterial agent administration is repeated periodically until the bacterial structures are eliminated from the patient's marrow cells and/or erythrocytes or both.

In addition, as noted previously, there are several causes for aplastic anemia. That being the case, the phrase "an aplastic anemia" is used herein to identify a disease state in which the patient has blood cells that contain one or more inclusions that stain with anti-*E. canis*, or antibodies to other *Ehrlichia* or *Anaplasma*.

The present disclosure provides the only known clinical observation of successful treatment of leukemia with a rifamycin in a patient with intractable recurrent acute lymphatic leukemia. Identification of a bacterial agent associated with aplastic anemia and end stage bone marrow failure has implicated an *Ehrlichia*-like agent, and this was the basis for the use of the antibiotic in end stage bone marrow failure in leukemia.

Clinical studies of treatment of leukemia with a rifamycin have not been reported. The rationale for use here is a limited investigation of organisms in leukemia, lupus, aplastic anemia, a myelodysplastic syndrome, and lymphomas. These studies have shown evidence for infections with organisms like the *Anaplasma*/Ehrlichiae, in many clinical situations, but most studies have not been controlled. The site of infection appears to be in the bone marrow, but largely seen in the megakaryocytes Little or nothing is known about the use of a rifamycin in treating human leukemia, although uncontrolled treatment of other syndromes has been done. Because the organism observed clinically is intracellular, the schedules appropriate for the treatment of intracellular tuberculosis were empirically chosen.

In one aspect of the invention, the leukemia or aplastic anemia patient is treated by administration of an antibacterial agent that is comprised of an antibacterial amount of a rifamycin alone or an antibacterial amount of a rifamycin along with an antibacterial amount of a possible synergistic antimicrobial agent.

The phrase "a rifamycin" is meant to include rifamycin itself as well as rifamycin derivatives as are discussed below. Rifamycin is a broad-spectrum antibiotic produced by *Streptomyces mediterranei* that is active against most gram-positive organisms and has variable activity against gram-negative organisms such as *Escherichia coli* and *Pseudomonas*. Rifamycin and its derivatives also have intracellular bactericidal activity.

Rifampin is a particularly preferred rifamycin derivative that is available from Aventis as RIFADIN®, and can administered per orally or by injection in an antibacterial amount. Capsules for oral administration are available that contain 150 or 300 mg of rifampin per capsule. Usual adult oral administrations are 600 mg once per day, usually with water about two hour before a meal, with dosages of about 450 to about 900 mg per day being contemplated. Combination therapeutics sold by Aventis under the name RIFATER® and RIFAMATE® can also be used. RIFATER® contains rifampin (120 mg), isoniazid (50 mg) and pyrazinamide (300 mg). RIFAMATE® is a combination of isoniazid (150 mg) and rifampin (300 mg). These combination drugs are usually used to treat tuberculosis.

Rifabutin, available under the trademark MYCOBUTIN® from Pharmacia-Upjohn (Now Pfizer), is also a preferred rifamycin derivative. Rifapentine, available from Aventis under the trademark PRIFTIN®, and rifamide are other rifamycin derivatives that can also be used.

It is to be understood that the rifampin need not be administered via the above-noted commercially available forms. Rather, those drugs can be compounded into a composition for administration to a SLE patient using well-known pharmaceutical techniques.

In another aspect of the invention, the leukemia or aplastic anemia patient is treated by administration of an antibacterial agent that is comprised of an antibacterial amount of a quinolone. Quinolone compounds typically contain two fused 6-membered rings that are aromatic and include a ring nitrogen atom having a keto group directly across the ring. The first quinolone, nalidixic acid, contains two ring nitrogen atoms, is effective against Gram (−) bacteria. Nalidixic acid was first marketed in 1965 and is still available.

The quinolones are divided into generations based on their antibacterial spectrum. The earlier generation agents exhibit, in general, a narrower spectrum of activity than the later ones. As will be noticed from the list below, several quinolones have been withdrawn from the market. These withdrawals have been because of adverse side effects. However, in view of the lethality of the diseases discussed herein, the prescribing physician may elect to treat using a pharmaceutical that has been withdrawn from general usage.

| Quinolone Generations |
|---|
| 1st Generation |
| cinoxacin |
| nalidixic acid |
| oxolinic acid |
| piromidic acid |
| pipemidic acid |
| rosoxacin |
| 2nd Generation |
| ciprofloxacin |
| enoxacin |
| fleroxacin (withdrawn) |
| lomefloxacin |
| nadifloxacin |
| norfloxacin |
| ofloxacin |
| pefloxacin |
| rufloxacin |

-continued

Quinolone Generations

3rd generation balofloxacin
gatifloxacin (withdrawn)
grepafloxacin (withdrawn)
levofloxacin
moxifloxacin
pazufloxacin
sparfloxacin
temafloxacin (withdrawn)

4th generation clinafloxacin
garenoxacin
gemifloxacin
prulifloxacin
sitafloxacin
trovafloxacin (withdrawn)

Ciprofloxacin (cipro) is a second generation drug within the quinolone class, specifically the fluoroquinolones. It is used to treat bacterial infections in various parts of the body when given orally and is a preferred quinolone for use herein.

One way to assess how long to continue administration of an above-noted drug is to continue administration until the stainable, phase contrast microscopically visible, exogenous bacterial structures seen in the patient's erythrocytes and/or marrow cells prior to treatment are absent from those cells post treatment, and preferably until no further evidence of infection is present. This duration of administration can take as long as about 120 days, the average lifetime of an erythrocyte, or more. Periodically repeated administrations of drugs that encompass the average lifetime of an erythrocyte are thus contemplated and are preferred.

Probenecid, a drug that decreases renal excretion of some drugs such as those contemplated for use herein, can also be administered in conjunction with a before-mentioned antibacterial agent to provide its decreased renal excretion effect. It is to be understood that the antibacterial agent such as probenecid and rifampin need not be administered via the above-noted commercially available forms. Rather, those drugs can be compounded into a composition for administration to a leukemia or aplastic anemia patient using well-known pharmaceutical techniques.

HISTORY OF STUDY OF HEMOTROPHIC INFECTION AND INVOLVEMENT OF THE BONE MARROW BY THE BACTERIA OF THE GROUP: ANAPLASMA/EHRLCHIA, AND MEDICAL STUDIES AND RATIONALE FOR THE TREATMENT OF END STAGE LEUKEMIA BONE MARROW FAILURE WITH ANTIBIOTICS.

The genus *Ehrlichia* is extensively studied in veterinary medicine. Members of the genus cause an economically important infection of the erythrocytes of cattle. *Ehrlichia* infection of cattle produces a hemolytic anemia, economic losses, and an unusual syndrome of chronic rheumatoid illness in those animals considered too valuable for euthanization. The causative agent is *Anaplasma marginale*.

Another Ehrlichial disease of canines was first reported in North Africa, but is worldwide in distribution. It can produce a carrier state, but in susceptible animals, it produces an illness called Tropical Canine Pancytopenia. This disease is essentially an intractable, progressive fatal aplastic anemia. Its causative agent was well studied during the Vietnam War, and has been named *Ehrlichia canis*. [Wandragula L, and Ristic M., "Anaplasmosis" in Woldehewit Z. and Ristic M. Eds. *Rickettsial and Chlamydial Diseases of Domestic Animals*. Pergamon Press, Oxford, United Kingdom, 1993, Chapter 3, pages 65-88.]

Human disease associated with a presumed *Ehrlichia* was reported in a patient with idiopathic aplastic anemia in 1973. It was the first report of human infection with an Ehrlichial agent [Kallick et al., "Human Bone marrow failure associated with *Ehrlichia canis*", Presented at the Interscience Conference on Antimicrobial Agents and Chemotherapy, Washington DC, 1973, Abstract #1].

Later reports of several Ehrlichial agents associated with tick transmission have been described, and the resulting diseases derive their names from the characteristic blood cell parasitized. The best studied of these diseases is Human Granulocytic Ehrlichiosis. As the name implies, it is found in the peripheral circulation in granulocytes. The infective agent was originally called an *Ehrlichia*, but following the isolation of the causative agent, and molecular investigation, it was renamed *Anaplasma phagocytophylium*. [Dumler et al., *J. Infect Disease* 1996 173:1027-1030].

An association of *Haemobartonella*-like organisms with Systemic Lupus Erythematosus (SLE) was reported in 1972 [Kallick et al., *Nature*, New Biology 1972 236:145-146], and an antigenic relationship of SLE to *A. marginale* (AM) was confirmed in 1980 [Kallick et al., *Arthr. and Rheumat.*, 1980 23:197-205]. In that study, all of 22 patients with SLE had antibodies to AM. Evidence of deposits of antigen was also seen by fluorescent antibody in the glomeruli of a patient with lupus nephritis. Continued study by many investigators has established that most of these reported organisms are related antigenically [Casperson et al., *Infect. and Immuni.* 2002 70:1230-1234].

The single case of human aplastic anemia of interest here was reported in 1973 and involved a 52 year old Caucasian man, who suffered from idiopathic aplastic anemia [Kallick et al., "Human Bone marrow failure associated with *Ehrlichia canis*", Presented at the Interscience Conference on Antimicrobial Agents and Chemotherapy, Washington DC, 1973, Abstract #1]. Because of some clinical similarities to the canine syndrome of Tropical Canine Pancytopenia, this patient's blood was examined by a technique developed by Nyindo and Ristic. Although not used today, the technique involved use of the patient's own harvested monocytes. When separated and fed in a culture medium, the monocytes cling to an immersed glass slide. When fed with medium for 2 weeks, the monocytes, now macrophages, exhibited intracytoplasmic inclusions like morulae that stained with antibody to *E. canis*. (FIG. 1).

Figure 2:
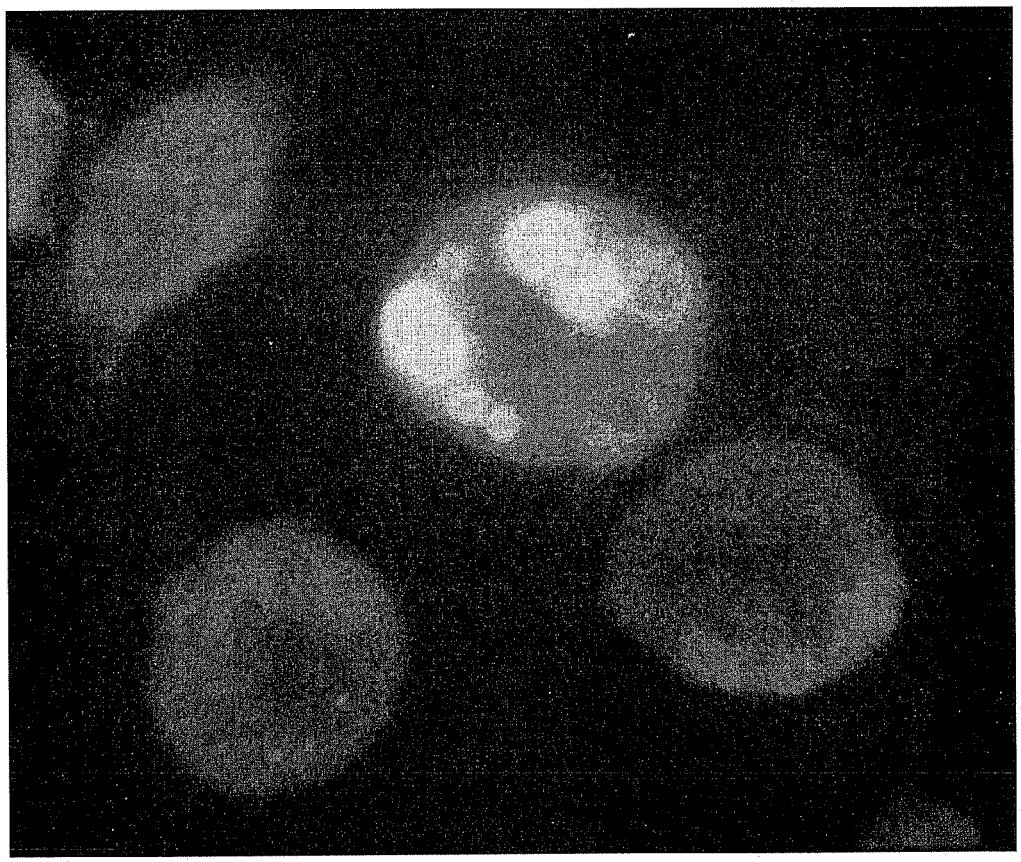
FIG. 2 is a photomicrograph of a rhesus monkey monocyte removed from the animal after injection of culture medium supernatant from the cells of FIG. 1 in to the animal and maintenance of the animal for several weeks.

The supernatant from that culture method was injected into a rhesus monkey, whose monocytes had been previously examined similarly for evidence of antigenically stained inclusions and found to be lacking such evidence. After several weeks of incubation, the monkey's macrophages had changed to exhibit similarly stained inclusions (FIG. 2) [Kallick et al., "Human Bone marrow failure associated with *Ehrlichia canis*", Presented at the Interscience Conference on Antimicrobial Agents and Chemotherapy, Washington DC, 1973, Abstract #1].

The single leukemia patient studied, and reported here, was a 64 year old Caucasian male who presented with acute lymphocytic leukemia (ALL), Philadelphia chromosome positive, who was converted to remission with a stem cell transplant from a matching brother. Within one year, the leukemia reverted to an active form, and he was treated with all anti-leukemic agents known, and these included several experimental agents from MD Anderson Hospital in Houston.

He developed diabetes associated with steroids, and right maxillary sinus infection with a species of *Mucorales*. He underwent debridement of his sinus, with removal of bone and tissue up to the floor of the left orbit. The sense of smell had been lost during the *mucor* infection. His condition worsened in the Houston hospital. He developed bone marrow failure, and was transferred by air ambulance in a bed to his home in the Chicago area with instructions for terminal hospice care. He was bedridden, unable to sit up, and appeared moribund.

The laboratory findings at that time included:

Hgb4 grams
WBC 900
Platelets 11K.

The present inventor, who is a physician, is a cousin of the patient. After informed consent, which included a description of the experience of the inventor, the patient was started on rifampicin (rifampin) 600 mg daily not within 2½ hours of meals. This treatment was not part of any protocol, but was a private request to the inventor.

Figure 3:
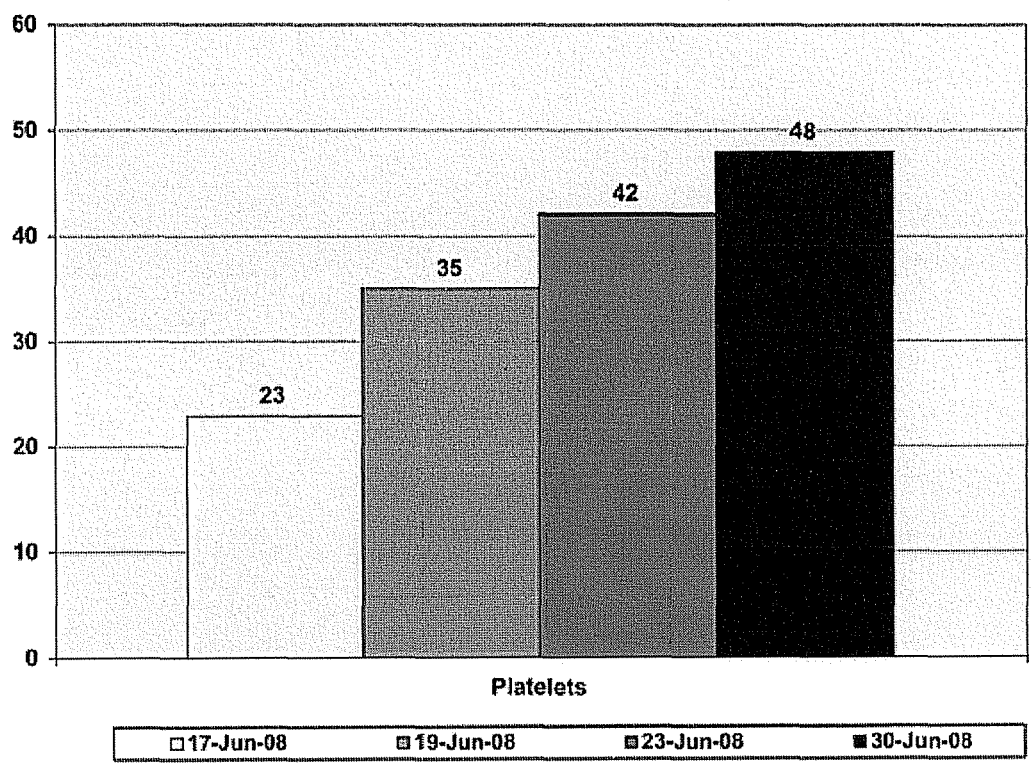
FIG. 3 is a graph showing the increase in platelet counts over time in a patient presenting with acute lymphocytic leukemia and treated with rifampicin.
Figure 4:
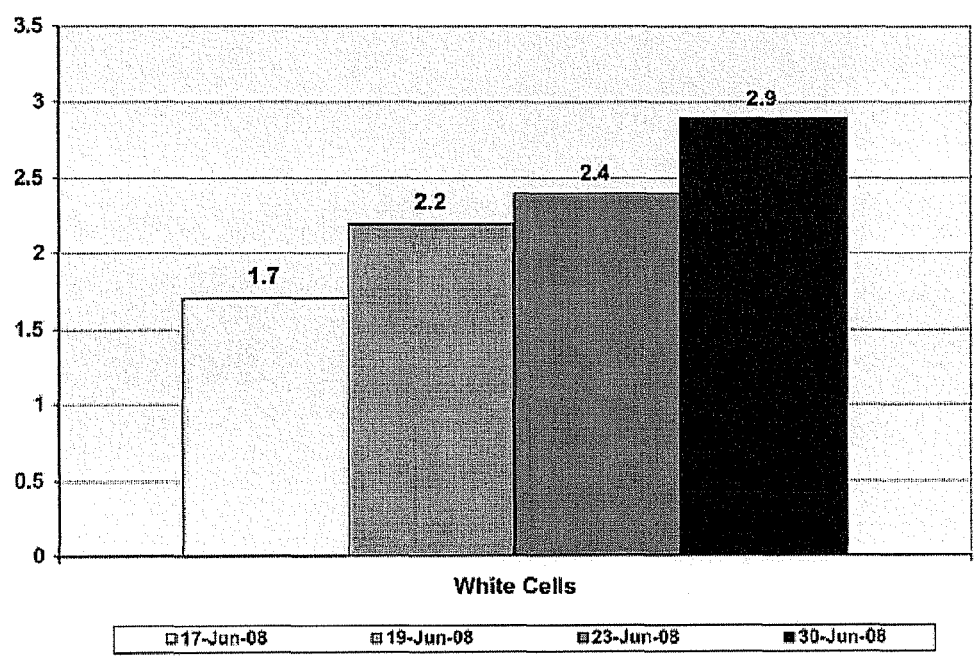
FIG. 4 is a graph showing the increase in white cell counts over the same time course in the patient of FIG. 3.
Figure 5:
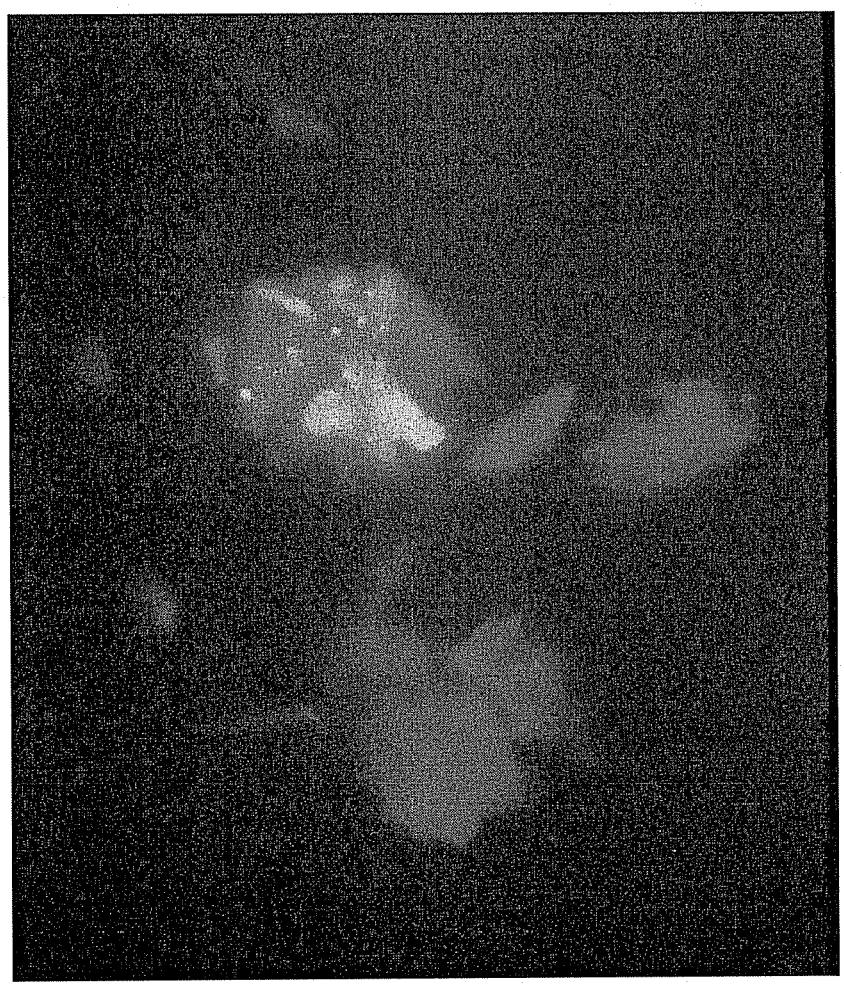

The patient began to show bone marrow recovery within 2 weeks, and within 6 weeks he had developed significant parameters of bone marrow remission (FIGS. 3, 4 and 5). With the improvement in laboratory studies, the patient showed marked clinical improvement with increase in strength, sitting, standing, and with short walks. He was in an area rehabilitation institution, and tolerating daily increases in physical activity. Unfortunately, blast cells had reappeared in the peripheral circulation, along with marked variations in platelets levels. Physical improvement continued.

The rifampicin was temporarily discontinued because of a transient drop in platelets that had previously risen to 48K, and this was suspiciously like the platelet agglutination rarely reported in rifampicin therapy. The rifampicin was later restarted, and continued at the original dosage.

Approximately 5 weeks after treatment began, the patient noted an abrupt onset of fatigue, hearing loss, and experienced a concomitant drop in platelets, but white cell levels (mature leukocytes and lymphocytes) continued at normal levels. He showed no evidence of progression of the *Mucor* process, and continued improvement. Within 10 days, however, he developed a skin rash, which appeared to be like those seen in infections of children with Cytomegalovus infection, developed a rapid central nervous system encephalopathy, and died of clinically diagnosed Cytomegalovirus disseminated infection. The inventor, as a medical attendant, believed that this was not related to the leukemia, but was possibly acquired from previously administered platelet transfusions.

Interpretation of Results:

The apparent recovery from end stage bone marrow failure after the extensive treatment of the usual inexorable progression of ALL, Philadelphia chromosome positive is remarkable, in that no other therapy had been given. Spontaneous remission is reported rarely in this clinical situation. The occurrence of apparent partial bone marrow remission in direct temporal conjunction with treatment of a suspected pathogen thought to be related to a pathogen previously reported in aplastic anemia, with one of the only two antibiotics (rifampicin), known to be active against the putative agent, is suggestive of a cause and effect event. It is thus believed that the causative agent in leukemias and some idiopathic pancytopenia is an *Anaplasma*/Ehrlichial agent related to most of the known bacteria in the *Anaplasma*/Ehrlichial group.

The ethical consideration here is because patients at the end stage of treatment of leukemia with bone marrow failure are almost all consigned to an imminent death, with no hope of remission. If such antibiotic treatment can alter that event, it is ethically appropriate to administer an antibiotic already marketed, but without that approved indication, but which has been given to hundreds of thousands for the therapy of tuberculosis.

Success in some or all of these cases, all of whom would make the choice of almost certain death or the possible chance of at least temporary remission, is ethically acceptable both to the investigation, and most likely to each subject. The success of this endeavor, permits the hematologist-oncologist to add another therapy to those already known, and can influence other investigations to explore the possible presence of *Anaplasma/Ehrlichia* in leukemia cases.

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. A process for treating a patient with leukemia or aplastic anemia having marrow cells and/or erythrocytes that contain inclusions that stain with anti-*E. canis* antibodies or antibodies to other *Ehrlichia* or *Anaplasma* that comprises administering to said patient an antibacterial agent that is comprised of an antibacterial amount of a rifamycin along with an antibacterial amount of a quinolone compound.

2. The process according to claim 1, wherein the antibiotic agent comprises a rifamycin that is rifampin, rifabutin or rifamide, and a quinolone compound that is selected from the group consisting of nalidixic acid, ciprofloxacin, levofloxacin, moxifloxacin, gatifloxacin, tefloxacin and trovafloxacin.

3. The process according to claim 1, wherein said rifamycin is rifampin or rifabutin.

4. The process according to claim 1, wherein said administrations are per oral.

5. The process according to claim 1, wherein said patient's marrow cells and/or erythrocytes contain bacterial structures stainable with acridine orange or giemsa and are visible in phase contrast microscopy.

6. The process according to claim 5, wherein said administration is repeated periodically until said bacterial structures are eliminated from the patient's marrow cells and/or erythrocytes or both.

7. The process according to claim 1, wherein said rifamycin is rifampin.

8. The process according to claim 7, wherein the amount of rifampin administered is about 600 mg daily.

9. A process for treating a patient with leukemia or aplastic anemia whose marrow cells and/or erythrocytes contain bacterial structures stainable with acridine orange or giemsa and are visible in phase contrast microscopy that comprises periodically administering to said patient an antibacterial amount of a quinolone.

10. The process according to claim 9, wherein said quinolone compound is selected from one or more of the group consisting of nalidixic acid, ciprofloxacin, levofloxacin, moxifloxacin, gatifloxacin, tefloxacin and trovafloxacin.

* * * * *